(12) United States Patent
Guimberteau et al.

(10) Patent No.: US 8,445,023 B2
(45) Date of Patent: May 21, 2013

(54) ANTI-MISUSE MICROPARTICULATE ORAL PHARMACEUTICAL FORM

(75) Inventors: Florence Guimberteau, Montussan (FR); Frederic Dargelas, Pessac (FR)

(73) Assignee: Flamel Technologies (FR)

( * ) Notice: Subject to any disclaimer, the term of this patent is extended or adjusted under 35 U.S.C. 154(b) by 335 days.

(21) Appl. No.: 12/638,739

(22) Filed: Dec. 15, 2009

(65) Prior Publication Data

US 2010/0092553 A1 Apr. 15, 2010

Related U.S. Application Data

(62) Division of application No. 11/439,432, filed on May 24, 2006.

(60) Provisional application No. 60/735,182, filed on Nov. 10, 2005.

(30) Foreign Application Priority Data

Nov. 10, 2005 (FR) ...................................... 05 53437

(51) Int. Cl.
*A61K 9/16* (2006.01)
(52) U.S. Cl.
USPC .......................................................... 424/490
(58) Field of Classification Search
None
See application file for complete search history.

(56) References Cited

U.S. PATENT DOCUMENTS

| | | | |
|---|---|---|---|
| 4,070,494 A | 1/1978 | Hoffmeister et al. | |
| 5,603,957 A * | 2/1997 | Burguiere et al. | 424/489 |
| 5,780,055 A | 7/1998 | Habib et al. | |
| 6,248,363 B1 | 6/2001 | Patel et al. | |
| 6,264,983 B1 | 7/2001 | Upadhyay | |
| 6,309,668 B1 | 10/2001 | Bastin et al. | |
| 6,444,246 B1 | 9/2002 | Popplewell et al. | |
| 6,566,560 B2 | 5/2003 | Travis | |

(Continued)

FOREIGN PATENT DOCUMENTS

| | | |
|---|---|---|
| EP | 0198769 | 10/1986 |
| EP | 0709087 | 5/1996 |

(Continued)

OTHER PUBLICATIONS

In the U.S. Patent and Trademark Office, Office Action in re: U.S. Appl. No. 11/651,577, dated Dec. 26, 2008, 22 pages.

(Continued)

*Primary Examiner* — Paul Dickinson
(74) *Attorney, Agent, or Firm* — Patton Boggs LLP

(57) ABSTRACT

The present invention relates to solid microparticulate oral pharmaceutical forms whose composition and structure make it possible to avoid misuse of the pharmaceutical active principle (AP) they contain.

The object of the present invention is to prevent solid oral drugs from being misappropriated for any use other than the therapeutic use(s) officially approved by the competent public health authorities. In other words, the object is to avoid the voluntary or involuntary misuse of solid oral drugs.

The invention relates to a solid oral pharmaceutical form which is characterized in that it contains anti-misuse means, in that at least part of the AP it comprises is contained in coated microparticles for modified release of the AP, and in that the coated microparticles of AP have a coating layer (Ra) which assures the modified release of the AP and simultaneously imparts crushing resistance to the coated microparticles of AP so as to avoid misuse.

31 Claims, 4 Drawing Sheets

U.S. PATENT DOCUMENTS

| | | |
|---|---|---|
| 6,696,088 B2 | 2/2004 | Oshlack et al. |
| 2002/0068365 A1 | 6/2002 | Kuhrts |
| 2003/0068276 A1 | 4/2003 | Hughes et al. |
| 2003/0068371 A1 | 4/2003 | Oshlack et al. |
| 2003/0068392 A1 | 4/2003 | Sackler |
| 2003/0083286 A1 | 5/2003 | Teng et al. |
| 2003/0118641 A1* | 6/2003 | Maloney et al. ............... 424/465 |
| 2003/0224051 A1 | 12/2003 | Fink et al. |
| 2004/0010984 A1 | 1/2004 | Wright |
| 2004/0022849 A1 | 2/2004 | Castan et al. |
| 2004/0052731 A1 | 3/2004 | Hirsh et al. |
| 2004/0053887 A1 | 3/2004 | Obae et al. |
| 2004/0126428 A1 | 7/2004 | Hughes et al. |
| 2004/0208936 A1 | 10/2004 | Chorin et al. |
| 2004/0228924 A1 | 11/2004 | Oshlack et al. |
| 2004/0234601 A1 | 11/2004 | Legrand et al. |
| 2005/0031546 A1 | 2/2005 | Bartholomaus et al. |
| 2005/0106249 A1* | 5/2005 | Hwang et al. .................. 424/469 |
| 2005/0163856 A1 | 7/2005 | Maloney et al. |
| 2005/0181046 A1 | 8/2005 | Oshlack et al. |
| 2005/0214223 A1 | 9/2005 | Bartholomaeus et al. |
| 2005/0266078 A1 | 12/2005 | Jorda et al. |
| 2005/0281748 A1 | 12/2005 | Hirsh et al. |
| 2007/0183980 A1 | 8/2007 | Arkenau-Maric et al. |
| 2007/0202049 A1 | 8/2007 | Guimberteau et al. |
| 2007/0224129 A1 | 9/2007 | Guimberteau et al. |
| 2007/0264326 A1 | 11/2007 | Guimberteau et al. |
| 2008/0008659 A1 | 1/2008 | Guimberteau et al. |
| 2008/0193540 A1 | 8/2008 | Soula et al. |
| 2009/0041838 A1 | 2/2009 | Guimberteau et al. |

FOREIGN PATENT DOCUMENTS

| | | |
|---|---|---|
| EP | 1293209 | 3/2003 |
| FR | 2 811 571 | 1/2002 |
| FR | 2 837 100 | 9/2003 |
| WO | WO-01/08661 | 2/2001 |
| WO | WO-03/013467 | 2/2003 |
| WO | WO-03/013479 | 2/2003 |
| WO | WO-03/013538 | 2/2003 |
| WO | WO-03/030878 | 4/2003 |
| WO | WO-03/077888 | 9/2003 |
| WO | WO-03/082204 | 10/2003 |
| WO | WO-03/103538 | 12/2003 |
| WO | WO-2004/004693 | 1/2004 |
| WO | WO-2004/10983 | 2/2004 |
| WO | WO-2004/10984 | 2/2004 |
| WO | WO-2004/026262 | 4/2004 |
| WO | WO-2004/037259 | 5/2004 |
| WO | WO-2004/052346 | 6/2004 |
| WO | WO-2004/054542 | 7/2004 |
| WO | WO-2005/016313 | 2/2005 |
| WO | WO-2005/016314 | 2/2005 |
| WO | WO-2005/079760 | 9/2005 |
| WO | WO-2006/056712 | 6/2006 |
| WO | WO-2006/056713 | 6/2006 |
| WO | WO-2006/089843 | 8/2006 |
| WO | WO-2006/125819 | 11/2006 |
| WO | WO-2006/133733 | 12/2006 |
| WO | WO-2006/134018 | 12/2006 |

OTHER PUBLICATIONS

In the U.S. Patent and Trademark Office, Final Office Action in re: U.S. Appl. No. 11/651,577, dated Jul. 31, 2009, 8 pages.
In the U.S. Patent and Trademark Office, Office Action in re: U.S. Appl. No. 11/651,577, dated Jan. 6, 2010, 7 pages.
In the U.S. Patent and Trademark Office, Final Office Action in re: U.S. Appl. No. 11/651,577, dated Jul. 9, 2010, 8 pages.
In the U.S. Patent and Trademark Office, Office Action in re: U.S. Appl. No. 11/651,577, dated Nov. 23, 2010, 13 pages.
In the U.S. Patent and Trademark Office, Final Office Action in re: U.S. Appl. No. 11/651,577, dated Apr. 29, 2011, 10 pages.
In the U.S. Patent and Trademark Office, Office Action in re: U.S. Appl. No. 11/791,336, dated Jun. 23, 2010, 14 pages.
In the U.S. Patent and Trademark Office, Final Office Action in re: U.S. Appl. No. 11/791,336, dated Dec. 8, 2010, 7 pages.
In the U.S. Patent and Trademark Office, Requirement for Restriction/Election in re: U.S. Appl. No. 11/651,577, dated Apr. 9, 2008, 7 pages.
In the U.S. Patent and Trademark Office, Requirement for Restriction/Election in re: U.S. Appl. No. 11/791,336, dated Feb. 16, 2010, 6 pages.
In the U.S. Patent and Trademark Office, Office Action in re: U.S. Appl. No. 11/439,432, dated Dec. 7, 2012, 8 pages.
In the U.S. Patent and Trademark Office, Final Office Action in re: U.S. Appl. No. 11/439,432, dated Feb. 29, 2012, 10 pages.
In the U.S. Patent and Trademark Office, Office Action in re: U.S. Appl. No. 11/439,432, dated Jul. 13, 2011, 6 pages.
In the U.S. Patent and Trademark Office, Final Office Action in re: U.S. Appl. No. 11/439,432, dated Dec. 22, 2009, 12 pages.
In the U.S. Patent and Trademark Office, Office Action in re: U.S. Appl. No. 11/439,432, dated Jan. 30, 3009, 21 pages.
In the U.S. Patent and Trademark Office, Requirement for Restriction/Election in re: U.S. Appl. No. 11/439,432, dated Apr. 29, 2008, 13 pages.
Remington's The Science and Practice of Pharmacy, 1995, 19th edition, Mack Publishing Co., Pennsylvania, USA.
New Pharmaceutical Forms: Technological, Biopharmaceutical and Medical Aspects, Buri, Puisieux, Doelker and Benoit 1985, pp. 175-227.

* cited by examiner (A): Observation with the naked eye (B): Observation under an optical microscope (A): Observation with the naked eye (B): Observation under an optical microscope

US 8,445,023 B2

ANTI-MISUSE MICROPARTICULATE ORAL PHARMACEUTICAL FORM

CLAIM FOR PRIORITY

This application is a divisional of U.S. application Ser. No. 11/439,432, filed May 24, 2006, which claims priority to U.S. Provisional Patent Application Ser. No. 60/735,182, filed Nov. 10, 2005, and FR 05/53437, filed Nov. 10, 2005; the contents of which are herein incorporated by reference in their entirety.

FIELD OF THE INVENTION

The present invention relates to solid microparticulate oral pharmaceutical formulations whose composition and structure make it possible to avoid misuse of the pharmaceutical or veterinary active principle (AP) they contain.

The active principles (AP) in question are pharmaceutical or veterinary AP, for example those classed in the category of stupefacient products, analgesics or narcotics. Misuse of these pharmaceutical active principles can give rise to drug addiction behavior.

In terms of the present disclosure, the expression "AP" denotes both a single active principle and a mixture of several active principles.

Microparticulate pharmaceutical formulation is understood in terms of the present invention as meaning any form in which the AP is contained in microparticles smaller than 1000 μm. These particles containing the AP can be coated microparticles for modified release of the AP. In the latter case, the microparticles are coated e.g. with a polymer film which controls the rate of release of the AP after oral administration.

PRESENTATION OF THE PROBLEM

The object of the present invention is to prevent solid oral drugs from being misappropriated for any use other than the therapeutic use(s) officially approved by the competent public health authorities. In other words, the object is to avoid the voluntary or involuntary misuse of solid oral drugs.

Misuse is mainly encountered in the following cases:
a) addictive behavior (drug addiction, doping),
b) criminal behavior (chemical subjection),
c) use of a drug in a manner that does not comply with the medical recommendations (dosage), due to carelessness or because of disabilities affecting the patient.

In case a. (or even in case b.), persons intending to misuse the solid oral drug will generally endeavor to extract the AP from the modified-release form to give a quick-acting form, and then:

either convert it to a pulverulent form by crushing so that it can be inhaled or swallowed, or convert it to a liquid form which can be injected with a syringe or swallowed.

The preparation of a liquid form from a solid oral drug involves an intermediate step for aqueous or organic extraction of the AP in question. This extraction is generally preceded by crushing.

The modes of administration by inhalation or injection are particularly suited to drug addicts because these are modes which make it possible to accentuate the effects of the AP and which favor its absorption in the organism over short periods of time. When the powder obtained by crushing is sniffed or dissolved in water and injected, the desired doping or euphoriant effects of the AP manifest themselves very rapidly and in an exacerbated manner.

At the present time there is also a particularly serious undesirable behavior which affects teenagers and concerns analgesic AP (aAP), more especially morphine and opium derivatives. In fact, teenagers prepare for their parties a cocktail of vodka with oxycodone, which they easily extract from the tablets with water and alcohol. This process consists in crushing the tablet and pouring the powder into a glass of vodka or water and then waiting for a sufficient time to completely extract the morphine derivatives, which can subsequently be absorbed.

Solid oral drugs can also be misused by chewing the drug before swallowing it, instead of swallowing it quickly in accordance with the dosage instructions.

The risks associated with addictive behavior (a.) and criminal behavior (b.) are obvious. It is pointed out that the misuse of drugs by injection is worse: the excipients can be responsible for local tissue necrosis, infections, and respiratory and cardiac disorders.

As regards the misuse of a drug associated with carelessness and/or the patient's disabilities (c.), this can also have serious consequences. For example, the chewing of modified-release forms of AP before swallowing converts the drug to an immediate-release form. Thus at best the drug will become ineffective after a very short time, and at worst it will become toxic.

There is therefore clearly a serious public health problem associated with the misuse of drugs, particularly solid oral drugs and especially those based on analgesics or narcotics. This growing phenomenon is of ever greater concern to the health authorities, especially in the United States and Europe, who are increasingly appealing for the development of pharmaceutical formulations that prevent misappropriation.

PRIOR ART

U.S. Pat. No. 6,696,088 relates to a multiparticulate oral pharmaceutical formulation that is indicated as being resistant to misuse. It comprises particles of opioid agonist AP in a modified-release form and particles containing an opioid antagonist. The form containing the antagonist is described as releasing less than 36%, and preferably less than 6.2%, of the antagonist AP over a period of 36 h. The two types of particles are interdispersed.

When misuse is being practiced, the consequence of crushing the microparticles to extract the opioid AP is to release the AP and its antagonist immediately and concomitantly and thereby to limit the desired effects of the misappropriated opioid.

As we understand it, said invention is based on the use of an active substance other than the AP and does not propose, inter alia, a solution for reducing the impact of crushing or reducing the extraction of the AP.

Patent application US-A-2003/0068371 describes an oral pharmaceutical formulation comprising an opiate AP (oxycodone), an antagonist of this AP (naloxone) and a gelling agent (e.g. xanthan gum). In particular, said US patent application discloses matrix granules of AP comprising lactose, xanthan gum, povidone and an outer coating based on EUDRAGIT RS 30D®/triacetin/antagonist. The gelling agent is presented as giving the formulation a viscosity such that it cannot be administered nasally or parenterally. As we understand it, this answer is inadequate because, according to said invention, the use of an antagonist is, inter alia, obligatory. Finally, this formulation contains no anti-crushing means, so it can be converted to a pulverulent form and consequently be the subject of misuse by the nasal or oral route.

Patent application WO-A-03/013479 describes an oral pharmaceutical formulation comprising an opiate analgesic and an opiate antagonist (naltrexone) in a pharmaceutically effective amount, together with a bitterness promoter. When the drug addict crushes the tablet, the opioid and its antagonist are released. The opioid effect is then neutralized. As we understand it, this system does not make it possible, inter alia, to prevent selective extraction of the opioid with water, without crushing.

In general, resorting to antagonists is not without its disadvantages in respect of the possible medical risks run by the users and the risks of inhibition of the intended therapeutic effect.

Patent application WO-A-2004/054542 describes a semi-liquid oral pharmaceutical form. It takes the form of a capsule (for example gelatin capsule) comprising the AP in a matrix phase composed of a water-insoluble high-viscosity liquid (sucrose acetate isobutyrate) and a polymer (cellulose acetate butyrate) that supposedly forms a network in the liquid phase. The formulation can optionally comprise a compound that modifies the rheology of the pharmaceutical form, and a solvent. By varying the different compounds and the concentration of the formulation, the authors state that they are able to modify the plasma profiles of the AP (oxycodone base) administered to dogs. As we understand it, this reference provides no solution for hindering, inter alia, misuse by injection, all the less because the viscosity of this formulation drops sharply with small additions of ethanol.

Patent application US-A-2003/0224051 describes an osmotic form for the modified release of oxycodone. This form consists of a tablet comprising a core of oxycodone or one of its salts, a semipermeable membrane enveloping at least part of the core, and an outlet orifice in the membrane to allow the release of the oxycodone. This type of tablet enables the opioid to be extracted easily by immersion in water for e.g. at least 12 hours. As we understand it, this tablet is not an appropriate solution to the problem of misuse.

Patent application EP-A-1 293 209 discloses an anti-misuse solid oral pharmaceutical formulation for the prolonged release of an opioid derivative (AP) contained in an ion exchange resin. The resulting AP/resin complex makes it possible to limit the plasma concentration obtained after misuse by chewing, inhalation or injection to a therapeutic concentration well below that sought by the misuser. The AP/resin complex takes the form of a matrix. As we understand it, no anti-crushing means is provided in the pharmaceutical formulation according to said prior art document. Furthermore, this pharmaceutical formulation contains no means for combating solvent extraction of the AP. It is therefore incapable of preventing solvent extraction of the AP, although the extraction time is longer than the normal release time of the AP. If this oral pharmaceutical formulation is left in a glass of water for 24 h, virtually all the AP is extracted.

Patent applications US-A-2003/0118641 and 2005/0163856 (=WO-A-01/08661) describe oral pharmaceutical formulations for the prolonged release of AP consisting of opioid compounds (analgesics) and their salts. These formulations supposedly prevent misuse by extraction of the AP with common solvents. These anti-misuse formulations do not contain antagonists, although this possibility can be envisaged in order to be even more dissuasive. These formulations comprise a mixture of:
a hydrophilic matrix agent (hydroxyalkyl cellulose) in an amount of 40-65% by weight;
an ion exchange resin (particles smaller than 50 μm in an amount of 5-15% by weight);
and at least one opiate AP.

After the incorporation of conventional compression additives, this mixture is converted to tablets.

This is therefore a macroscopic matrix system comprising particles of ion exchange resin complexed with the AP, and an anti-extraction means consisting of a viscosifier, preferably hydroxypropyl methyl cellulose. As we understand it, this system is capable of improvement, especially in terms of anti-misuse efficacy.

Intermediate patent document WO-A-2005/079760 discloses a pharmaceutical formulation consisting of rubbery microparticles of AP obtained by extrusion, permitting prolonged release of the AP and having anti-misuse properties. These extruded microparticles comprise a matrix formed of an inert poly(ethyl acrylate/methyl methacrylate) copolymer: EUDRAGIT® NE 30D or NE 40D. This matrix contains the AP (oxycodone), another Eudragit®, RS PO, a plasticizer and a lubricant.

Misuse is prevented by an anti-crushing means that only involves the rubbery character of the matrix particles for modified release of the AP. As we understand it, no means is provided for combating extraction of the AP in a solvent medium.

As we understand the prior art, none of the anti-misuse solutions proposed hitherto is satisfactory, especially in terms of preventing abusive extraction of the AP with water, alcohol or other potable solvents.

OBJECTS OF THE INVENTION

Under these circumstances, one of the objects of the present invention is to overcome the inadequacies of the prior art.

Another object of the invention is to provide novel solid oral drugs whose misuse will be made difficult, if not impossible, especially for cases (a.)(b.)(c.) referred to above, preferably without resorting to substances, other than the AP, that are capable of being pharmaceutically active and hence dangerous for the users, or even AP inhibitors, for example AP antagonists.

Another object of the invention is to provide novel solid oral drugs whose misuse will be made difficult, if not impossible, especially for cases (a.)(b.)(c.) referred to above, even after a "long" liquid extraction of the AP (e.g. an analgesic). In terms of the present disclosure, a "long" liquid extraction is an extraction lasting more than 10 min.

Another object of the invention is to provide novel solid oral drugs that prevent misuse by short liquid extraction and/or crushing.

Another object of the invention is to provide novel solid oral drugs having the following characteristics:
under normal conditions of administration, these solid oral drugs have a therapeutic effect for e.g. 12 or 24 hours;
any attempt at abusive extraction of the AP (e.g. an analgesic) will cause the drug to be converted to a form such that, after it has been ingested, rapid absorption of the AP in the blood stream will be impossible.

Another object of the invention is to provide novel solid oral drugs which:
can easily be administered to patients who have difficulties in swallowing large tablets, for example seriously ill patients, infants or children;
make it possible to associate several AP in one and the same dosage unit, even if these AP are not mutually compatible and/or do not have the same release kinetics;
can exist in forms which can be administered one or more times a day and in which it is possible easily and independently to adjust the release rate and time of different AP.

Another object of the invention is to provide novel solid oral drugs whose in vitro dissolution profile is independent of the dose of AP.

Another object of the invention is to provide novel solid oral drugs which make it possible to avoid fraudulent misappropriation of the properties of the AP they contain by preventing any conversion of the drug to a form that can be taken orally, nasally and/or by injection (intravenously, subcutaneously, intramuscularly, etc.) outside the therapeutic limits. This would prevent or at least greatly reduce the risks associated with this undesirable behavior.

Another object of the invention is to provide novel solid oral drugs that make it possible to avoid misuse while at the same time guaranteeing that the patient undergoing normal follow-up has a quality of treatment and, in particular, a dose that conform to his needs.

Another object of the invention is to provide novel solid oral drugs that make it possible to avoid misuse without affecting the pharmacological properties of the drug, without causing the patient who uses the drug normally to run additional risks, and finally without detracting from the patient's comfort when the drug is administered.

Another object of the invention is to provide novel solid oral drugs that can be administered one or more times a day and limit the risks of damage to the tissues due to local overconcentrations of AP.

Another object of the invention is to provide novel solid oral drugs which can take a variety of galenical forms such as tablets, powder sachets, capsules and the like.

Another object of the invention is to provide novel anti-misuse solid oral drugs which are easy and economic to prepare.

BRIEF DESCRIPTION OF THE INVENTION

To achieve these objects, it is to the inventors' credit to have reformulated the general problem of the misuse of pharmaceutical formulations.

If the different illicit modes of administration of an active principle are examined, it seems in fact that crushing of the dry form is usually an obligatory step.

In the case of misuse by nasal administration, the dry pharmaceutical formulation first has to be converted to a pulverulent powder suitable for sniffing. Crushing of the pharmaceutical formulation is therefore certainly an obligatory step.

In the case of misuse by the oral administration of a prolonged-release dry form, it is necessary to accelerate the release of the active principle by finely crushing the microparticles or the tablet.

In the case of misuse by parenteral administration, the AP first has to be extracted into a liquid phase, which in practice is water or organic solvents, to a sufficiently high concentration to avoid injecting excessively large volumes, e.g. greater than 1 ml. This extraction step is facilitated by a previous step in which the dry form is crushed so that the active principle can be dissolved or suspended. Moreover, after this extraction phase, misuse is only possible if the viscosity of the liquid is not too high (e.g. less than or equal to 100 mPa·s).

Thus the crushing of a dry form is also an obligatory step for misuse of said pharmaceutical formulation by parenteral administration.

It is to the Applicant's credit to have reformulated the problem of combating the misuse of dry pharmaceutical formulations by characterizing a primary problem (a) of preventing crushing of the system containing the AP;

and a secondary problem (b) of preventing misuse of the AP after its possible extraction.

This novel approach enabled the Applicant to discover, surprisingly and unexpectedly, that it is appropriate to incorporate, into the composition of the drug whose misuse it is sought to prevent, the AP in the form of coated microparticles for modified release of the AP and, optionally, a combination of pharmaceutically acceptable excipients, in microparticulate or non-microparticulate form, whose physicochemical mode of action makes it possible to thwart any voluntary or involuntary act of misuse, or even render it impossible.

Thus the invention relates mainly to a solid oral pharmaceutical formulation which is characterized in that it contains anti-misuse means, in that at least part of the AP it comprises is contained in coated microparticles for modified release of the AP, and in that the coated microparticles of AP have a coating layer (Ra) which assures the modified release of the AP and simultaneously imparts crushing resistance to the coated microparticles of AP so as to avoid misuse.

The pharmaceutical formulation according to the invention solves in particular the main problem presented and meets at least some of the objectives set, in an effective, simple and economic manner, with the aid of physicochemical means. The latter are totally inoffensive to the normal user. They are pharmacologically inert compounds that are approved by the pharmacopeia and by the public health authorities responsible for granting drug marketing authorizations.

In one preferred embodiment, the solid oral pharmaceutical formulation according to the invention contains, in addition to the anti-crushing coating layer (Ra), at least one viscosifier (Vb) that makes it very difficult, if not impossible, to extract the AP contained in the coated microparticles of AP so as to avoid misuse of the AP after liquid extraction.

In terms of the present disclosure, the expression "viscosifier" denotes both a single viscosifier and a mixture of several viscosifiers.

DETAILED DESCRIPTION OF THE INVENTION

According to the invention, at least part of the AP is in a modified-release form, namely in the form of coated microparticles for modified release of said AP.

The active principles (AP) considered in the present invention are pharmaceutical or veterinary AP, for example those classed in the category of analgesics or narcotics. Misuse of these AP can give rise to addiction behavior.

In terms of the present invention, the expression "AP" denotes one active principle or a mixture of several active principles.

In terms of the present invention, "microparticulate form" is understood as meaning any pharmaceutical formulation in which the AP is contained in microparticles smaller than 1000 microns. These particles containing the AP can be microparticles individually coated with a film for modified release of the AP. In the latter case, the microparticles are coated e.g. with a polymer-based film which controls the rate of release of the AP.

In the present disclosure, "modified-release form" denotes a form in which at least a fraction of the AP is released at a rate slower than that of an immediate-release form. This fraction can be e.g. between 1 and 100%, preferably between 10 and 100% and particularly preferably between 30 and 100%. In particular, a modified release can be prolonged and/or delayed and/or in the form of one or more release peaks (pulses). Modified-release formulations are well known in this field; cf., for example, Remington's *The science and practice of pharmacy*, 19th edition, Mack Publishing Co., Pennsylvania, USA.

In the present disclosure, "immediate-release form" denotes a form which releases the bulk of the AP it contains over a relatively short period, i.e. at least 70% of the AP is released in 1 hour, preferably in thirty minutes, at any pH between 1.4 and 6.8 in an in vitro dissolution test.

All the in vitro dissolution profiles referred to in the present disclosure are obtained as indicated in the European Pharmacopoeia 4th edition, entitled "Dissolution test for solid oral forms": type II dissolutest performed under SINK conditions at 37° C. and stirred at 75 rpm.

The pharmaceutical formulation according to the invention is therefore a formulation for modified release of the AP.

In terms of the invention, "pharmaceutical formulation" is to be understood in the broad sense, i.e. this phrase also encompasses veterinary and dietetic formulations.

This pharmaceutical formulation can also comprise one or more forms for immediate release of the AP.

Advantageously, the pharmaceutical formulation according to the invention, which is novel in its structure, presentation and composition, can exist e.g. in the form of a tablet, a powder sachet, a multidose reconstitutable suspension powder sachet, or a capsule.

Coated Microparticles of AP

The coated microparticles for modified release of the AP are advantageously microparticles that are each coated with at least one coating (comprising e.g. at least one polymer) deposited by the techniques known to those skilled in the art. The following work, for example, may be consulted on this question: *Formes pharmaceutiques nouvelles: aspects technologique, biopharmaceutique et médical* (*New pharmaceutical formulations: technological, biopharmaceutical and medical aspects*) by Buri, Puisieux, Doelker and Benoit, éditions Lavoisier 1985, pages 175 to 227.

In other words, these coated microparticles preferably each consist of a core comprising AP and a coating comprising at least one coating layer that envelops the core (preferably entirely) and governs the modified release (preferably continuous) of the AP. This release takes place when the coated microparticles of AP are brought into contact with the gastrointestinal juices.

The uncoated microparticles of AP (i.e. before coating) can be e.g.:
    inert cores covered with at least one layer containing AP;
    or microparticles of pure AP;
    or granules formed of a matrix of supporting excipients, including the AP.

In the case of supported granules, the inert core or support can be composed of sucrose and/or saccharose and/or dextrose and/or lactose and/or a sucrose/starch mixture. The inert core or support can also be a cellulose microsphere or any other particle of pharmaceutically acceptable excipient. Particles of xanthan gum, guar gum, calcium phosphate or calcium carbonate may be mentioned as non-limiting examples of inert supports. Their mean diameter can be between 10 and 200 microns, between 20 and 150 microns or between 50 and 100 microns.

These coated microparticles of the "reservoir" type (or individually coated microparticles) can be likened to vehicles for the transport and release of at least one AP in the small intestine or even the large intestine.

Examples which may be mentioned of coated microparticles for modified release of the AP are those described in the following patent documents: EP-B-0 709 087 and WO-A-03/030878.

Coating on the Microparticles of AP

Advantageously, the coated microparticles of AP comprise at least one coating layer (Ra), preferably only one coating layer (Ra), which assures the modified release of the AP and simultaneously imparts crushing resistance to the coated microparticles of AP so as to avoid misuse.

Particularly preferably, the coating layer (Ra) is designed in such a way that, in the event of crushing, it allows maintenance of a non-immediate (i.e. modified) release for at least some of the coated microparticles for modified release of the AP.

The crushing envisaged here can be e.g. any crushing performed by the techniques normally employed by misusers, namely, in particular: mortar/pestle, coffee grinder, between two spoons, by crunching/chewing, etc.

In one valuable embodiment, the coating layer (Ra) is designed in such a way that, in the event of crushing, it allows maintenance of a modified release for at least 40%, preferably at least 60% and particularly preferably at least 80% of the coated microparticles for modified release of the AP.

Preferably, the anti-crushing coating layer (Ra) comprises:
    (A1) at least one film-forming (co)polymer (A1) insoluble in the gastrointestinal juices;
    (A2) at least one (co)polymer (A2) soluble in the gastrointestinal juices;
    (A3) at least one plasticizer (A3);
    (A4) optionally at least one surfactant and/or lubricant and/or mineral and/or organic filler (A4).

According to a purely illustrative and non-limiting selection of the invention:
    (A1) is selected from the group comprising:
    water-insoluble cellulose derivatives, preferably ethyl cellulose and/or cellulose acetate,
    acrylic polymers, e.g. copolymers of (meth)acrylic acid and an alkyl (e.g. methyl) ester, copolymers of an acrylic and methacrylic acid ester carrying at least one quaternary ammonium group (preferably at least one copolymer of an alkyl (meth)acrylate and trimethylammonioethyl methacrylate chloride), and more precisely the products marketed under the trademark EUDRAGIT® RS and/or RL,
    polyvinyl acetates,
    and mixtures thereof;
    (A2) is selected from the group comprising:
    nitrogen-containing (co)polymers, preferably from the group comprising poly-acrylamides, poly-N-vinylamides, polyvinylpyrrolidones (PVP) and poly-N-vinyl-lactams,
    water-soluble cellulose derivatives,
    polyvinyl alcohols (PVA),
    polyalkylene oxides, preferably polyethylene oxides (PEO),
    polyethylene glycols (PEG),
    and mixtures thereof,
PVP being particularly preferred;
    (A3) is selected from the group comprising:
    cetyl alcohol esters,
    glycerol and its esters, preferably from the following subgroup: acetylated glycerides, glycerol monostearate, glyceryl triacetate and glycerol tributyrate,
    phthalates, preferably from the following subgroup: dibutyl phthalate, diethyl phthalate, dimethyl phthalate, dioctyl phthalate,
    citrates, preferably from the following subgroup: acetyl tributyl citrate, acetyl triethyl citrate, tributyl citrate, triethyl citrate,
    sebacates, preferably from the following subgroup: diethyl sebacate, dibutyl sebacate,
    adipates, azelates,
benzoates,
vegetable oils,
fumarates, preferably diethyl fumarate,
malates, preferably diethyl malate,
oxalates, preferably diethyl oxalate,
succinates, preferably dibutyl succinate,
butyrates,
cetyl alcohol esters,
salicylic acid,
triacetin,
malonates, preferably diethyl malonate,
castor oil (this being particularly preferred),
and mixtures thereof.

(A4) is selected from the group comprising:
anionic surfactants, preferably from the subgroup comprising alkali metal or alkaline earth metal salts of fatty acids, stearic and/or oleic acid being preferred,
and/or non-ionic surfactants, preferably from the following subgroup:
polyethoxylated oils, preferably polyethoxylated hydrogenated castor oil,
polyoxyethylene/polyoxypropylene copolymers,
polyethoxylated sorbitan esters,
polyethoxylated castor oil derivatives,
stearates, preferably calcium, magnesium, aluminum or zinc stearates,
stearylfumarates, preferably sodium stearylfumarate,
glycerol behenates,
talcum,
colloidal silica,
titanium oxide, magnesium oxide,
bentonite,
microcrystalline cellulose,
kaolin,
aluminum silicate,
and mixtures thereof.

In addition to the qualitative parameters defining the coated microparticles according to the invention, it can be specified that, according to an advantageous quantitative modality, the coating layer (Ra) comprises the following in % by weight, based on the total weight of the coating:

$10 \leq A1 \leq 90$, preferably $15 \leq A1 \leq 80$ and particularly preferably $60 \leq A1 \leq 80$;

$5 \leq A2 \leq 50$, preferably $10 \leq A2 \leq 40$ and particularly preferably $10 \leq A2 \leq 25$;

$1 \leq A3 \leq 30$, preferably $2 \leq A3 \leq 20$ and particularly preferably $5 \leq A3 \leq 15$;

$0 \leq A4 \leq 40$, preferably $0 \leq A4 \leq 30$ and particularly preferably $0 \leq A4 \leq 20$, the sum of the percentages being equal to 100.

Furthermore, the release rate is regulated for example in the following manner:
by control of the thickness of the coating (Ra);
by the weight ratios between the components A1, A2, A3 and optionally A4 of the coating (Ra).

Advantageously, the coating on the coated microparticles for modified release of the AP can comprise, in addition to the essential constituents A1, A2, A3 and optionally A4, other conventional ingredients known to those skilled in the art, such as, in particular, colorants, pigments, preservatives, flavorings, etc., and mixtures thereof.

Another noteworthy characteristic of the coating (Ra) on the coated microparticles is the fact that the coating layer (Ra) represents a fraction by weight Tp, expressed in % by dry weight, based on the total weight of the coated microparticles, such that: $Tp \geq 15$, Tp preferably being between 30 and 60, particularly preferably between 40 and 60 and very particularly preferably between 45 and 55 or about 50.

Without wishing to be bound by theory, this relatively high coating rate enables the coating layer (Ra) to assure the modified release of the AP and simultaneously to impart crushing resistance to the coated microparticles of AP so as to avoid misuse.

Without implying a limitation, the preferred coated microparticles of AP according to the invention are those having a mean diameter less than or equal to 1000 µm, preferably of between 50 and 800 µm, particularly preferably of between 100 and 600 µm and very particularly preferably of between 100 and 300 µm.

Unless indicated otherwise, the diameters of microparticles referred to in the present disclosure are mean diameters by volume.

As regards the preparation of the coated microparticles, the techniques that are advantageously used for depositing the coating for modified release of the AP, or depositing the active layer based on the AP, are techniques known to those skilled in the art, for example the technique of spray coating in a fluidized air bed, wet granulation, compaction or extrusion/spheronization.

Outer Coating

In one particular variant of the invention, the coated microparticles for modified release of the AP have an outer coating designed in such a way that, in the manufacture of tablets, it contributes to maintaining a modified release for at least some of said coated microparticles of AP for modified release of the AP. The outer coating is composed of at least one deformable organic constituent with a melting point of between 40° C. and 120° C., preferably of between 45° C. and 100° C.

In one preferred variant, the outer coating comprises at least 10% by weight of deformable organic constituent.

In particular, in one variant of the invention, the deformable organic constituent included in the outer coating is selected from polyalkylene glycols, particular preference being given to polyethylene glycols with a molecular weight of 6,000 to 20,000 D.

In another variant, the deformable organic constituent of the outer coating is a fat or mixture of fats selected e.g. from the group of fats comprising hydrogenated vegetable oils, fatty acids, fatty alcohols, fatty acid and/or fatty alcohol esters, polyolefins, and mineral, vegetable, animal or synthetic waxes, particular preference being given to fatty acid esters such as diglycerides and triglycerides and mixtures thereof, glycerol behenate and hydrogenated castor, soya, cottonseed and palm oils.

In one additional variant, the outer coating comprises:
a mineral filler, for example silica or titanium dioxide, or an organic filler, for example microcrystalline cellulose,
and/or at least one lubricant, for example magnesium stearate or sodium benzoate,
and/or at least one hydrophilic polymer such as water-soluble cellulose derivatives, synthetic polymers, preferably polyvinylpyrrolidone, acrylic and methacrylic polymers or polyvinyl alcohols (PVA),
and/or at least one surfactant.

Preferably, the outer coating represents from 5 to 50%, preferably from 10 to 30% and particularly preferably in the order of 20% by dry weight, based on the total weight of the overcoated microparticles of AP.

The expression "overcoated microparticle" denotes a coated microparticle of AP that also comprises an outer coating as defined above, i.e. an outer coating which, in the manufacture of tablets, contributes to maintaining a modified release for at least some of said coated microparticles of AP for modified release of the AP.

Additional information on the outer coating can be found in published patent application WO-A-03/077888.

Viscosifier (Vb)

Preferably, the viscosifier (Vb) is selected from those which are soluble in at least one of the following solvents: water, alcohols, ketones and mixtures thereof, said viscosifier(s) being capable of increasing the viscosity of the extraction liquid so as to thwart misuse, especially by injection.

"Water" is understood as meaning any aqueous solvent such as water stricto sensu or any aqueous solution, for example of an organic acid (e.g. acetic acid), saline solutions, sodas or drinks. "Alcohols" are understood as meaning any alcohols taken on their own or in a mixture with one another. "Ketones" are understood as meaning any ketones taken on their own or in a mixture with one another.

Particularly preferably, the viscosifier (Vb) is selected from the following groups of polymers:
  polyacrylic acids and derivatives thereof, and/or
  polyalkylene glycols (e.g. polyethylene glycol), and/or
  polyalkylene oxides (e.g. polyethylene oxides), and/or
  polyvinylpyrrolidones, and/or
  gelatins, and/or
  polysaccharides, preferably from the subgroup comprising sodium alginate, pectins, guars, xanthans, carrageenans, gellans and cellulose derivatives (e.g. hydroxypropyl methyl cellulose, methyl cellulose, hydroxyethyl cellulose, carboxymethyl cellulose),
  and mixtures thereof.

According to one modality of the invention, the viscosifier Vb is a polyoxyethylene with a high molecular weight, e.g. with a molecular weight of 1 million g/mol to 8 million g/mol, for example of 2 million, 5 million or 7 million g/mol.

Preferably, the viscosifier Vb, e.g. the high-molecular polyoxyethylene, is included in microparticles distinct from the microparticles of AP.

Particularly preferably, the microparticles of AP and the microparticles of viscosifier Vb have a similar size distribution and a similar density and are inseparable by sieving.

According to one preferred modality, the viscosifier (Vb) is capable of increasing the viscosity of the liquid used for possible extraction so as to trap the extracted AP in the viscous medium.

This viscosifier (Vb) makes it possible to increase the viscosity of the extraction liquid e.g. to beyond 100 mPa·s, preferably 200 mPa·s, particularly preferably beyond 500 mPa·s and very particularly preferably 1000 mPa·s.

It is also to the Applicant's credit to have proposed, in one variant, viscosifiers (Vb) that are effective in the case of both aqueous phase extraction and organic solvent extraction. Advantageously, these viscosifiers (Vb) are mixtures of hydrophilic compounds and hydrophobic compounds so as to ensure that the extraction liquid has a high viscosity (above 100 mPa·s, for example), whether it be aqueous or organic.

As far as the amount of viscosifier (Vb) is concerned, this can easily be determined by those skilled in the art. Said amount corresponds to the minimum amount necessary to bring the viscosity of 2.5 ml of extraction liquid to a value greater than or equal to 100 mPa·s.

In several variants which can be combined with one another, in the pharmaceutical formulation according to the invention at least one viscosifier (Vb) is present:
  in and/or on microparticles,
  and/or in an outer coating on all or some of the microparticles of AP,
  and/or in the free state, i.e. neither contained in nor supported by microparticles.

Advantageously, at least part of the viscosifier is in the form of micro-particles that are inseparable from the coated or uncoated microparticles of AP.

Excipients in the Free State

The pharmaceutical formulation can optionally contain one or more pharmaceutically acceptable excipients in the free state, i.e. neither contained in nor supported by microparticles of AP, said excipient contributing to the crushing resistance of the coated microparticles of AP.

Preferably, these excipients contributing to the crushing resistance of the coated microparticles of AP are selected from the group comprising:
  calcium stearate;
  glycerol palmitostearate;
  magnesium oxide;
  polyalkylene glycols, e.g. polyethylene glycols;
  polyvinyl alcohol;
  sodium benzoate;
  stearic acid;
  maize starch;
  talcum;
  colloidal silica;
  zinc stearate, magnesium stearate;
  stearylfumarate;
  and mixtures thereof.

In alternative embodiments of the invention, at least part of the viscosifier is:
  in the free state, i.e. neither contained in nor supported by coated or uncoated microparticles of AP (alternative 1), or
  in the form of microparticles that are distinct from the coated or uncoated microparticles of AP (alternative 2).

Advantageously, in alternative 2, the microparticles of viscosifier are inseparable from the coated or uncoated microparticles of AP. In terms of the present disclosure, the expression "inseparable" means e.g. inseparable by conventional means such as sieving or centrifugation.

In alternative 2, the viscosifier is e.g.:
  in and/or on microparticles,
  and/or in an outer coating on all or some of the microparticles of AP.

Still in alternative 2, the microparticles comprising the viscosifier are preferably physically indiscernible from the microparticles of AP so that they cannot easily be sorted by any appropriate physical means. The microparticles comprising the viscosifier are indiscernible from the microparticles of AP especially by having the same size and/or same density and/or same shape and/or same color.

In another alternative, the viscosifier is e.g.:
  in and/or on microparticles,
  and/or in an outer coating on all or some of the microparticles of AP.

In one preferred embodiment, the pharmaceutical formulation according to the invention is multimicroparticulate. If this pharmaceutical formulation comprises microparticles of AP (e.g. aAP) and microparticles of viscosifier (Vb), said microparticles preferably have a similar size distribution and a similar density and are preferably inseparable by sieving. Thus the microparticles of viscosifier cannot be separated from the coated or uncoated microparticles of AP.

In another preferred embodiment, the pharmaceutical formulation according to the invention is multimicroparticulate. If this pharmaceutical formulation comprises microparticles of AP (e.g. aAP) and microparticles of viscosifier (Vb), said microparticles preferably have the same size distribution and the same density and are preferably inseparable by sieving.

Thus the microparticles of viscosifier cannot be separated from the coated or uncoated microparticles of AP.

Sequestering Agent Q

Obviously, in the case where the microparticulate pharmaceutical formulation comprises at least one salt of at least one analgesic active principle, those skilled in the art may add at least one sequestering agent to said pharmaceutical formulation so as to form a poorly soluble complex with the AP in solution in an aqueous or aqueous-alcoholic drink.

The sequestering agent is e.g. a salt whose ion of opposite polarity to that of the AP is preferably an organic ion. Thus, for a cationic active principle, this sequestering agent is e.g. an organic salt like sodium docusate, or an anionic polymer. The sequestering agent can also be e.g. a salt of an ion exchange resin.

In terms of the present invention, a sequestering agent Q is present in the pharmaceutical formulation in a free form, i.e. non-complexed. "Non-complexed" means that no complex or chemical interaction exists between the sequestering agent Q and the salt of the active principle, AP, in the solid pharmaceutical form.

If the AP salt and the sequestering agent Q are present simultaneously in a solvent, e.g. in the case of an illicit attempt to extract the AP, the sequestering agent Q is capable of inducing complexation or a chemical interaction with the AP salt in said solvent. In terms of the present invention, the sequestering agent Q is considered to be "capable of inducing complexation" with the AP salt if the sequestering agent Q is capable of inducing complexation of the AP salt in at least one customary solvent selected from water and aqueous solutions such as water/ethanol mixtures, alcohol, alcoholic drinks, sodas, vinegar, hydrogen peroxide and mixtures thereof. Advantageously, the sequestering agent Q is capable of inducing complexation of the AP salt in more than one of these customary solvents.

The sequestering agents Q used to trap the AP, especially analgesic AP, are inoffensive, even when used regularly. These products are inert from the pharmacological point of view and are approved by the various pharmacopeias and drug registration authorities.

In one pharmaceutical formulation according to the invention, at least one sequestering agent Q is present:

in microparticles devoid of AP, and/or on microparticles, and/or in the free state, i.e. neither contained in nor supported by microparticles.

Preferably, in one pharmaceutical formulation according to the invention, the sequestering agent Q is present in a first phase separate from at least one second phase, said second phase containing at least one AP salt. For example, the pharmaceutical formulation comprises microparticles of AP salt and microparticles of sequestering agent Q that are distinct. Advantageously, said microparticles have a similar size distribution the a similar density and are inseparable by sieving.

Preferably, the sequestering agent Q comprises a salt containing ions capable of forming a complex with the AP in solution. These ions are preferably organic ions of opposite polarity to that of the AP in solution: if the AP is in anionic form in solution, the sequestering agent Q comprises an organic cation, a metal cation or a mixture thereof. Likewise, if the AP is in cationic form in solution, the sequestering agent Q comprises an organic anion.

For example, the following salts containing an organic anion may be mentioned:

anionic organic salts such as sodium dodecylsulfate or sodium docusate;

anionic polymers such as (meth)acrylic copolymers (e.g. Eudragit® S and Eudragit® L), crosslinked polyacrylic acids (e.g. Carbopol), carboxymethyl cellulose and derivatives thereof, crosslinked carboxymethyl cellulose and derivatives thereof, and other polysaccharides (e.g. alginate, xanthan gum or gum arabic), and alginate/(sulfonate) propylene glycol;

monovalent or polyvalent salts such as glucuronates, citrates, acetates, carbonates, gluconates, succinates, phosphates, glycerophosphates, lactates, trisilicates, fumarates, adipates, benzoates, salicylates, tartrates, sulfonamides and acesulfames;

saponified fatty acids such as acetic, succinic, citric, stearic and palmitic acid salts and self-emulsifying glyceryl monooleates;

polyamino acids, proteins or peptides, such as albumins, caseins, globulins and enzymes;

and mixtures thereof.

In another embodiment, the ion of opposite polarity to that of the AP in solution is an organic metal cation or a mixture thereof. For example, the following salts containing an organic or metal cation may be mentioned:

cationic salts, e.g. of the metals Ca, Fe, Mg or Zn, in the form of acesulfames, acetates, adipates, benzoates, carbonates, chlorides, citrates, fluorides, fumarates, gluconates, glucuronates, glycerophosphates, hydroxides, iodates, iodides, lactates, oxides, phosphates, trisilicates, salicylates, succinates, sulfonamides or tartrates;

organic cationic salts such as quaternary ammonium salts, particularly trimethyl-tetradecylammonium bromide or benzethonium chloride;

cationic polymers such as chitosan and (meth)acrylic copolymers (e.g. Eudragit® RS, Eudragit® RL or Eudragit® E);

polyamino acids, proteins or peptides;

and mixtures thereof.

The sequestering agent Q can be an ion exchange resin, preferably a strongly acidic cation exchange resin when the AP is cationic, or a strongly basic anion exchange resin when the AP is anionic. Advantageously, such an ion exchange resin is contained in a first phase separate from a second phase containing the AP.

In one embodiment of the invention, the ion exchange resin is e.g. a derivative of a styrene/divinylbenzene copolymer.

In one embodiment of the invention, the strongly acidic cation exchange resin will be e.g. a derivative of a sulfonated styrene/divinylbenzene copolymer, such as Amberlite® IRP69, Amberlite® IR69F (Rohm and Haas), Amberlite 200, Amberlite 200C (Rohm and Haas) or Dowex 88 (Dow) and the like.

In one embodiment of the invention, the strongly basic anion exchange resin will be selected e.g. from derivatives of styrene/divinylbenzene copolymers carrying quaternary ammonium groups, such as Duolite® AP143 (Rohm and Haas), Amberlite IRA958, Amberlite IRP67 (Rohm and Haas) and DOWEX 22 (Dow).

The sequestering agent Q in the form of resin can also be selected from crosslinked methacrylic acid/divinylbenzene copolymers or one of their salts, such as Amberlite® IRP88, Amberlite® IRP64 (Rohm and Haas) and DOWEX MAC-3 (Dow).

The sequestering agent Q in the form of ion exchange resin can also be selected from phenolic polyamines such as Amberlite® IRP58 (Rohm and Haas), and mixtures thereof.

In one embodiment of the invention, the sequestering agent Q in the form of ion exchange resin is in a first phase separate from at least one second phase, said second phase comprising the AP salt. For example, the sequestering agent Q in the form of ion exchange resin is contained in microparticles distinct from the microparticles comprising the AP salt. The microparticles of AP and the microparticles of sequestering agent Q in the form of ion exchange resin can be in a form such that they have a similar size distribution, a similar density and are inseparable by sieving.

In a first preferred mode of carrying out the invention, the sequestering agent Q is selected from:

anionic organic salts such as sodium dodecylsulfate or sodium docusate;

cationic organic salts such as quaternary ammonium salts, particularly trimethyl-tetradecylammonium bromide or benzethonium chloride;

and strongly acidic cation exchange resins or strongly basic anion exchange resins, depending on the polarity of the AP.

In a second preferred mode of carrying out the invention, the sequestering agent Q is selected from:

the strongly acidic cation exchange resins Amberlite® IRP69, Amberlite® IR69F (Rohm and Haas), Amberlite 200, Amberlite 200C (Rohm and Haas) or Dowex 88 (Dow), and mixtures thereof, when the AP is cationic;

and the strongly basic anion exchange resins Duolite® AP143 (Rohm and Haas), Amberlite IRA958, Amberlite IRP67 (Rohm and Haas) and DOWEX 22 (Dow), and mixtures thereof, when the AP is anionic.

The amount of agent Q is adapted by those skilled in the art by calculating the amount of ionic charge required to trap all or part of the dose of AP contained in the unit form. The amount of sequestering agent Q must be able to complex enough AP for the remaining amount of free AP in solution to be insufficient to achieve the desired effect in the event of illicit use. Preferably, the amount of sequestering agent Q is sufficient to complex all the AP from the unit dose.

In one variant, the pharmaceutical formulation can also be a monolithic form (e.g. tablet).

In one embodiment, the pharmaceutical formulation according to the invention comprises microparticles of viscosifier V and/or microparticles of sequestering agent Q, preferably microparticles of viscosifier V and microparticles of sequestering agent Q. In this embodiment, the microparticles of viscosifier V and the microparticles of sequestering agent Q are distinct from the microparticles of AP.

In another embodiment of the invention, the pharmaceutical formulation comprises microparticles of AP as well as microparticles of viscosifier V and/or microparticles of sequestering agent Q. Preferably, the pharmaceutical formulation comprises these three types of microparticles, i.e. microparticles of AP, microparticles of viscosifier V and microparticles of sequestering agent Q, in one and the same unit form. Advantageously, these microparticles have a similar size distribution and a similar density and are inseparable from one another by sieving.

In a first variant, the pharmaceutical formulation according to the invention cannot be converted to a dry form with immediate release of the AP which can be administered by sniffing.

In a second variant, the pharmaceutical formulation according to the invention cannot be converted to an injectable form with immediate release of the AP.

In a third variant, the pharmaceutical formulation according to the invention comprises modified-release AP and optionally immediate-release AP. This variant can be combined with the first and second variants referred to above, which means that, in a pharmaceutical formulation containing modified-release AP and immediate-release AP, the modified-release AP cannot be converted to a dry form which can be administered by sniffing or to an immediate-release injectable form.

In a fourth variant, the pharmaceutical formulation according to the invention is characterized in that extraction of the AP by chewing and/or crushing is not effective.

In a fifth variant, the pharmaceutical formulation according to the invention is characterized in that it is devoid of AP antagonist(s).

In a sixth variant, the pharmaceutical formulation according to the invention is characterized in that it comprises at least one AP antagonist. With knowledge of the AP used, those skilled in the art can easily determine the appropriate antagonist(s).

Of course, any combination of at least two of these six variants is included in the present invention (except combination of the fifth and sixth variants).

Active Principle(s)

The AP used belongs e.g. to at least one of the following families of active substances: amphetamines, analgesics, anorexigenics, antalgics, antidepressants, antiepileptics, antimigraine substances, antiparkinsonism substances, antitussives, anxiolytics, barbiturates, benzodiazepines, hypnotics, laxatives, neuroleptics, opiates, psychostimulants, psychotropic substances, sedatives and stimulants. In the case where the AP is an analgesic AP (aAP), it is preferably an opioid.

Even more precisely, the AP used is selected from the following compounds: anileridine, acetorphine, acetyl-alpha-methylfentanyl, acetyldihydro-codeine, acetylmethadol, alfentanil, allylprodine, alpha-cetylmethadol, alpha-meprodine, alpha-prodine, alpha-methadol, alpha-methylfentanyl, alpha-methylthiofentanyl, atropine, butorphanol, benzethidine, benzylmorphine, beta-hydroxyfentanyl, beta-hydroxymethyl-3-fentanyl, beta-cetylmethadol, beta-meprodine, beta-methadol, beta-prodine, bezitramide, buprenorphine, dioxaphenyl butyrate, clonitazene, cyclazocine, cannabis, cetobemidone, codeine, coca, cocaine, codoxime, dezocine, dimenoxadol, dipipanone, desomorphine, dextromoramide, dextropropoxyphene, diampromide, diethylthiambutene, difenoxin, dihydrocodeine, dihydroetorphine, dihydromorphine, dimenoxadol, dimepheptanol, dimethylthiambutene, diphenoxylate, drotebanol, eptazocine, ethoheptazine, ethylmethylthiambutene, ethylmorphine, etonitazene, ecgonine, ephedrine, etorphine, etoxeridine, fentanyl, furethidine, heroin, hydrocodone, hydromorphinol, hydromorphone, hydroxypethidine, isomethadone, ketobemidone, levallorphan, lofentanil, levomethorphan, levomoramide, levophenacylmorphan, levorphanol, meptazinol, meperidine, metazocine, methadone, methyldesorphine, methyl dihydromorphine, methylphenidate, methyl-3-thiofentanyl, methyl-3-fentanyl, metopon, moramide, morpheridine, morphine, myrophine, nalbuphine, narceine, nicomorphine, norlevorphanol, normethadone, nalorphine, normorphine, nicocodine, nicodicodine, nicomorphine, noracymethadol, norcodeine, norpipanone, opium, oxycodone, oxymorphone, papaveretum, phenadoxone, phenoperidine, promedol, properidine, propiram, propoxyphene, parafluorofentanyl, pentazocine, pethidine, phenampromide, phenazocine, phenomorphan, pholcodine, piminodine, piritramide, proheptazine, propanolol, racemethorphan, racemoramide, racemorphan, remifentanil, sufentanil, thebacon, thebaine, thiofentanyl, tilidine, trimeperidine, tramadol, their pharmacologically acceptable salts, esters, hydrates, polymorphs and isomers, and mixtures thereof.

The pharmaceutical formulation according to the invention can comprise at least one analgesic active principle (aAP) and at least one additional AP that is different from the aAP. This non-analgesic AP is preferably selected from the group comprising antidepressants, amphetamines, anorexics, non-analgesic painkillers, antiepileptics, antimigraine substances, antiparkinsonism substances, antitussives, anxiolytics, barbiturates, benzodiazepines, hypnotics, laxatives, neuroleptics, psychostimulants, psychotropic substances, sedatives, stimulants, anti-inflammatories, their pharmacologically acceptable salts, esters, hydrates, polymorphs and isomers, and mixtures thereof.

The following may be mentioned among the anti-inflammatory active principles that can be envisaged: ibuprofen, acetaminophen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, amineoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, their pharmacologically acceptable salts, esters, hydrates, polymorphs and isomers, and mixtures thereof.

Even more precisely, the analgesic AP used is selected from the group comprising oxycodone hydrochloride, morphine sulfate, oxymorphone hydro-chloride, hydromorphone hydrochloride, hydrocodone hydrochloride and tramadol hydrochloride.

In terms of the invention, the expression "pharmaceutical formulation" is understood in the broad sense, i.e. veterinary or dietetic formulations, in particular, are encompassed.

According to another of its features, the invention relates to a formulation which is characterized in that it comprises a plurality of microparticles (coated or uncoated microparticles of AP; optionally microparticles of viscosifier) as defined above, e.g. at least 500, preferably from 1,000 to 1,000,000 and particularly preferably from 5,000 to 500,000 microparticles.

According to another of its features, the invention relates to a pharmaceutical formulation comprising a plurality of populations of coated microparticles of AP, said populations being distinguished from one another by their release kinetics and/or the AP they contain.

Without implying a limitation, it must nevertheless be emphasized that the pharmaceutical formulation according to the invention is of particular value in that it can take the form of a single daily oral dose comprising from 500 to 500,000 microparticles, including the coated microparticles of AP.

Advantageously, the pharmaceutical formulation comprising coated micro-particles according to the invention is in a galenical form selected from the group comprising tablets (advantageously dispersible in the mouth or stomach), powders, suspensions, syrups, reconstitutable suspension powders, and capsules.

It may be interesting to mix, in one and the same capsule, one and the same tablet or one and the same powder, at least two types of coated microparticles of AP whose release kinetics are different but within the framework characteristic of the invention.

The invention further relates to the use of the coated microparticles described above for the manufacture of novel pharmaceutical formulations, particularly (but without implying a limitation) for the therapeutic treatment of pain.

The invention further relates to a method of therapeutic treatment which is characterized in that it consists in administering the pharmaceutical formulation as defined above to the patient.

The invention further relates to a method of therapeutic treatment which is characterized in that it consists in ingesting the pharmaceutical formulation as defined above according to a given dosage.

The invention further relates to a method for the therapeutic treatment of pain which is characterized in that it consists in administering the pharmaceutical formulation as defined above to the patient.

The invention further relates to a method for the therapeutic treatment of pain which is characterized in that it consists in ingesting the pharmaceutical formulation as defined above according to a given dosage, the AP used comprising at least one painkiller, e.g. an analgesic.

The invention further relates to a method of combating the misuse of AP which is characterized in that it consists essentially in using a pharmaceutical formulation as defined above.

The invention further relates to a method of combating the misuse of AP which is characterized in that it consists essentially in using, in a pharmaceutical form, coated microparticles of AP for modified release of the AP, said microparticles having a coating layer (Ra) which assures the modified release of the AP and simultaneously imparts crushing resistance to the coated microparticles of AP so as to avoid misuse, and optionally at least one viscosifier (Vb) capable of preventing extraction of the AP contained in the coated microparticles of AP so as to avoid misuse.

Advantageously, the coating layer (Ra) and the viscosifier (Vb), if present, are as defined above.

The invention will be explained more clearly by means of the Examples below, given solely by way of illustration, which afford a clear understanding of the invention and demonstrate its different embodiments and/or modes of implementation, as well as its different advantages.

EXAMPLES

The reference dissolution test in the Examples which follow is an in vitro dissolution test performed as indicated in the European Pharmacopoeia 5th edition, entitled "Dissolution test for solid oral forms": type II dissolutest performed under SINK conditions, maintained at 37° C. and stirred at 75 rpm in 900 ml of 0.1 N HCl medium.

Example 1

Microparticles of Oxycodone HCl According to the Invention

A mixture of 1600 g of oxycodone HCl, 100 g of Klucel® EF (hydroxy-propyl cellulose/Aqualon) and 12,052 g of water is film-coated onto 300 g of inert cellulose beads (Asahi-Kasei) in a GPCG1 fluidized air bed (Glatt®). 450 g of the resulting granules are then coated with a mixture composed of 315 g of ethyl cellulose (Ethocel 20 Premium/DOW), 81 g of povidone (Plasdone PVP K29/32/ISP), 36 g of castor oil, 18 g of Cremophor RH 40 (macrogolglyceroli hydroxystearas/BASF) and 12,020 g of ethanol.

Figure 1:
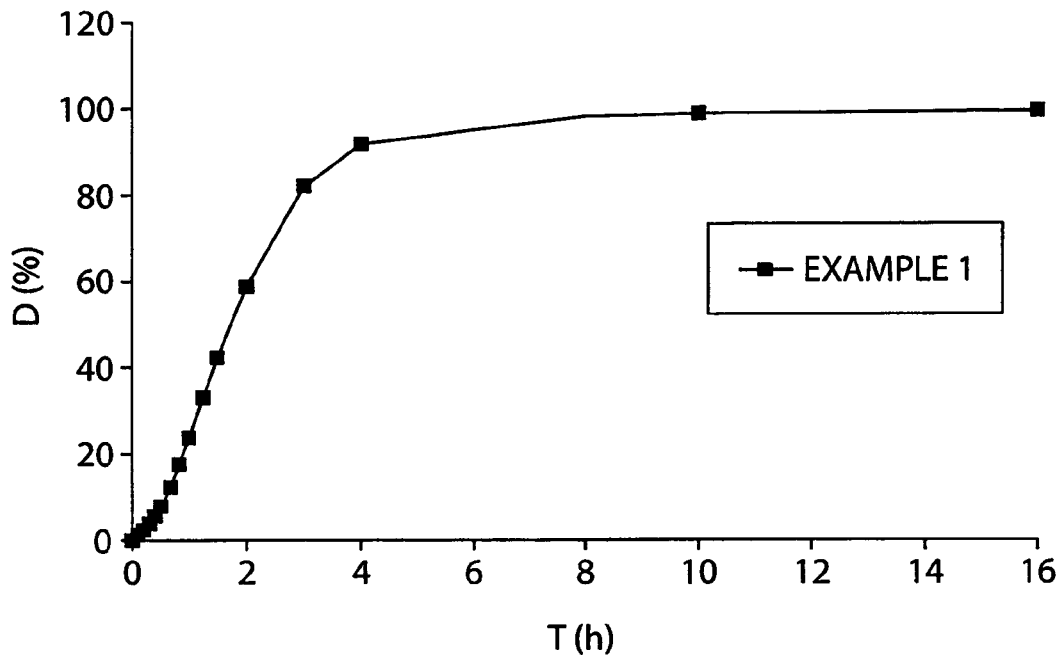
FIG. 1 shows the dissolution profile in an in vitro reference test (% dissolution D as a function of time T) on the microparticles of Example 1: -■-.

The coating represents 50% of the weight of the microparticle and assures that the active principle is released over about 4 h, as shown in FIG. 1. The release profile is determined under the conditions of the reference dissolution test.

Example 2

Crushing of the Microparticles of Oxycodone HCl Prepared According to Example 1

200 mg of microparticles prepared in Example 1 (i.e. a dose of 80 mg of oxycodone HCl) are crushed by different methods representing different possible ways of misuse:
  (a) by crushing vigorously for 2 minutes (~120 rotations) with a pestle and mortar (250 ml),
  (b) by pressing 8 times between two spoons,
  (c) by using an "LGS pulverizer" tablet mill (LGS Health Products, USA),
  (d) by using a coffee grinder for 30 seconds.

Figure 2:
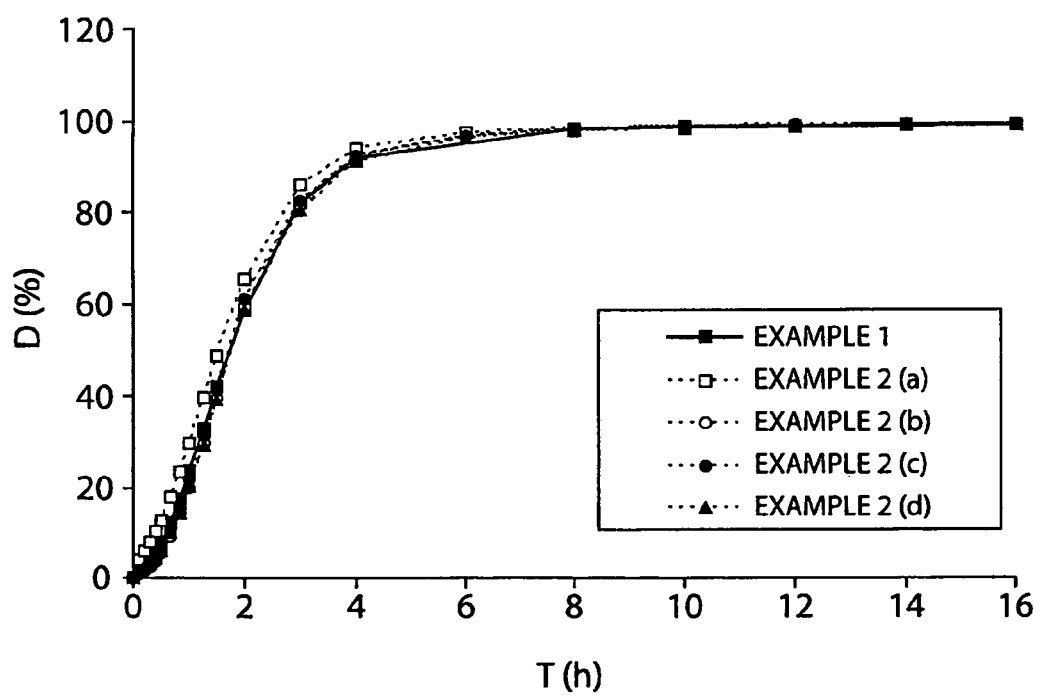
FIG. 2 shows the dissolution profile in an in vitro reference test (% dissolution D as a function of time T) on the microparticles of Example 1: -■-, and Example 2: (a) ---□---, (b) ---○---, (c) ---●---, (d) ---▲---.

The release profiles of the crushed microparticles are shown in FIG. 2. The release profile is determined under the conditions of the reference dissolution test.

The release profiles of Example 1 (intact microparticles) and Example 2 (crushed microparticles) are similar in terms of the test for the f2 similarity factor (f2>50), calculated as indicated by the FDA (Guidance for Industry SUPAC-MR: Modified release solid oral dosage forms, p. 32).

Thus crushing has little or even no effect on the release of the oxycodone from the microparticles.

Example 3

Appearance of the Contents of a Capsule According to the Invention 200 mg of microparticles prepared in Example 1 (i.e. a dose of 80 mg of oxycodone HCl) are mixed with the following viscosifiers: 90 mg of Klucel HF (hydroxypropyl cellulose/Aqualon), 20 mg of PolyOx WSR 303 Sentry (poly-ethylene oxide/Dow) and 20 mg of Xantural 180 (xanthan/cpKelco) previously sieved to between 100 and 600 µm. The whole is incorporated into a size 0 gelatin capsule.

Figure 3:
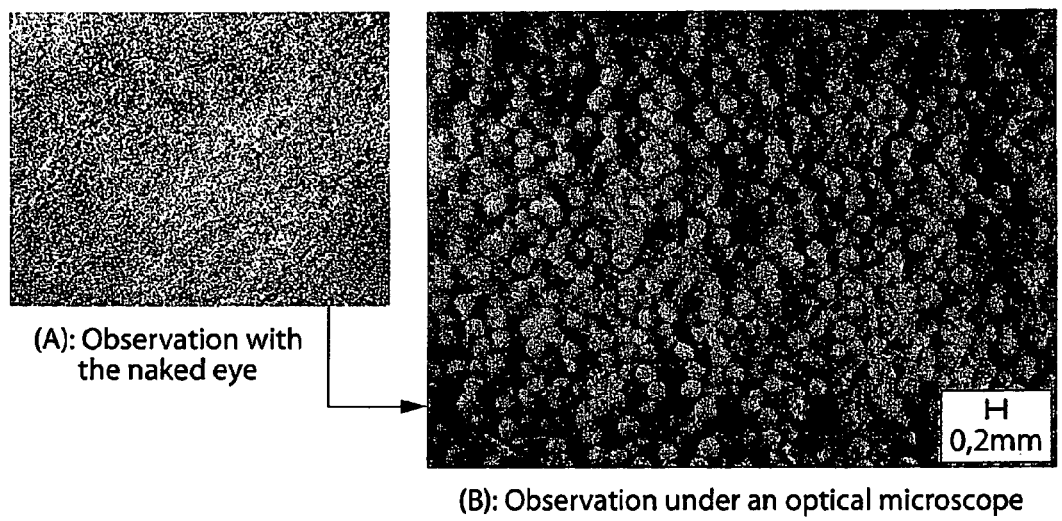
FIG. 3 shows photographs of the contents of a capsule according to Example 3, observed with the naked eye (A) and under an optical microscope (B).

FIG. 3 shows photographs of the contents of the capsule, observed with the naked eye (A) and under an optical microscope (B).

As shown in FIG. 3(A), observed with the naked eye, the microparticles of active principle and the microparticles of viscosifiers are:
  indistinguishable,
  inseparable by sieving.

In the photograph of FIG. 3(B) obtained by optical microscopy (note scale), there are only two distinct populations of particles: on the one hand spherical microparticles of oxycodone HCl and microparticles of two viscosifiers, and on the other hand rod-shaped particles of a 3rd viscosifier. Given the very small size of these particles (about 0.2 mm), they cannot be separated from one another.

Example 4

Test for Syringe Extraction of a Form According to the Invention 200 mg of microparticles prepared in Example 1 (i.e. a dose of 80 mg of oxycodone HCl) are mixed with 90 mg of Klucel HF (hydroxypropyl cellulose/Aqualon), 20 mg of PolyOx WSR 303 Sentry (polyethylene oxide/Dow) and 20 mg of Xantural 180 (xanthan/cpKelco) previously sieved to between 100 and 600 µm. The whole is incorporated into a size 0 gelatin capsule.

The capsule is opened and the contents are crushed according to Example 2(a) with a mortar and pestle and then mixed for 10 min with 2.5 ml of extraction liquid at ambient temperature or at the boil. The solution is then taken up with a 2.5 ml syringe (with an 18G needle) through cotton wool serving as a filter. The amount of oxycodone HCl extracted is analyzed by HPLC or UV and is shown in Table 1.

The low extraction yields observed (<20%) are totally dissuasive for potential misusers.

Example 5

Test for Syringe Extraction of a Form According to the Invention 200 mg of microparticles prepared in Example 1 (i.e. a dose of 80 mg of oxycodone HCl) are mixed with 150 mg of Klucel HXF (hydroxypropyl cellulose/Aqualon), 50 mg of PolyOx WSR 303 Sentry (polyethylene oxide/Dow) and 30 mg of Carbopol 971P (carbomer/BF Goodrich). The mixture is incorporated into a size 00 gelatin capsule.

The capsule is opened and the contents are crushed according to Example 2(a) with a mortar and pestle and then mixed for 10 min with 10 ml of extraction liquid at ambient temperature or at the boil. The solution is then taken up with a 10 ml syringe (with an 18G needle) through cotton wool serving as a filter. The amount of oxycodone HCl extracted is analyzed by HPLC or UV and is shown in Table 2.

The low extraction yields observed (<20%) are totally dissuasive for potential misusers.

Example 6

Test for Syringe Extraction of a Form According to the Invention 150 g of Klucel HXF (hydroxypropyl cellulose/Aqualon), 50 g of PolyOx WSR 303 Sentry (polyethylene oxide/Dow), 30 g of Carbopol 971P (carbomer/BF Goodrich) and 10 g of povidone (Plasdone PVP K29/32/ISP) are wet-granulated on a MiPro apparatus. The granules are passed through a 100-600 µm sieve.

250 mg of the resulting granules are added to 200 mg of microparticles prepared in Example 1 (i.e. a dose of 80 mg of oxycodone HCl). The whole is incorporated into a size 0 gelatin capsule. The capsule is opened and the contents are crushed according to Example 2(a) with a mortar and pestle and then mixed for 10 min with 10 ml of extraction liquid at ambient temperature or at the boil. The solution is then taken up with a 10 ml syringe (with an 18G needle) through cotton wool serving as a filter. The amount of oxycodone HCl extracted is analyzed by HPLC or UV and is shown in Table 3.

The low extraction yields observed (<20%) are totally dissuasive for potential misusers.

Example 7

Manufacture of a Tablet According to the Invention 200 g of microparticles prepared in Example 1 are mixed with 90 g of Klucel HF (hydroxypropyl cellulose/Aqualon), 20 g of PolyOx WSR 303 Sentry (polyethylene oxide/Dow), 20 g of Xanthural 180 (xanthan/cpKelco), 100 g of lactose (Tablettose/Meggle GmbH), 10 g of magnesium stearate (Brenntag AG) and 30 g of croscarmellose sodium (Ac-Di-Sol/FMC Bipolymer).

470 mg tablets (i.e. a dose of oxycodone of 80 mg) are manufactured using a Korsch reciprocating press.

The tablet obtained is crushed according to Example 2(a) with a mortar and pestle and then mixed for 10 min with 2.5 ml of extraction liquid at ambient temperature or at the boil. The solution is then taken up with a 2.5 ml syringe (with an 18G needle) through cotton wool serving as a filter. The amount of oxycodone HCl extracted is analyzed by HPLC or UV and is shown in Table 4.

The low extraction yields observed (<20%) are totally dissuasive for potential misusers.

Example 8

Microparticles of Oxycodone HCl According to the Invention

Step 1: Granules
1615 g of oxycodone and 85 g of povidone (Plasdone® K29-32/ISP) are dispersed in a mixture containing 2052 g of water and 1105 g of ethanol. The solution is sprayed onto 300 g of cellulose spheres (Asahi-Kasei) in a Glatt GPCG1 fluidized air bed.

Step 2: Anti-Crushing Microparticles 315 g of ethyl cellulose (Ethocel 20 Premium/Dow), 81 g of povidone (Plasdone K29-32/ISP), 18 g of macrogolglyceroli hydroxystearas (Cremophor RH40/BASF) and 36 g of castor oil (Garbit huilerie) are solubilized in a mixture composed of 3105 g of acetone and 2070 g of isopropanol. This solution is sprayed onto 450 g of granules (prepared in step 1).

Figure 4:
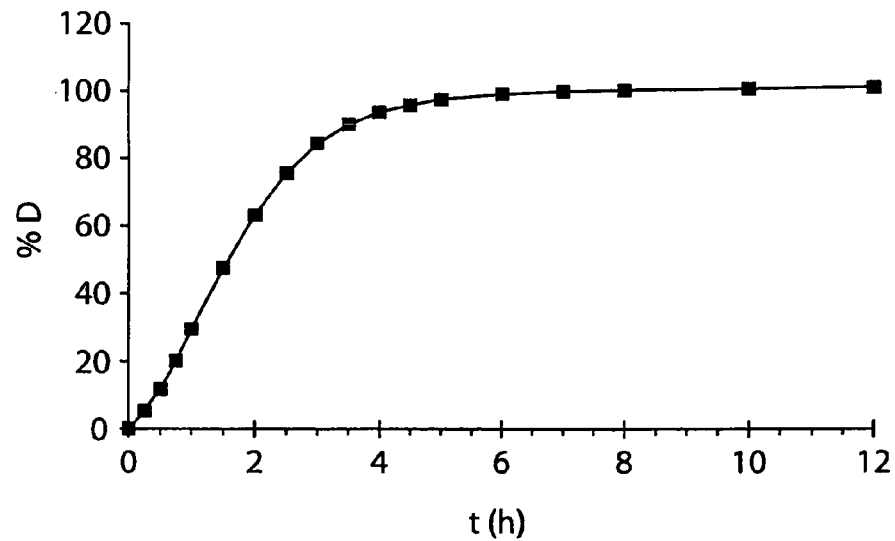
FIG. 4 shows the release profile (% by weight of aAP as a function of time in hours) of microcapsules in 0.1 N HCl (Example 8).

The coating represents 50% of the weight of the microparticle and assures that the is released as shown in FIG. 4. The release profile is determined under the conditions of the reference dissolution test.

Example 9

Contents of a Capsule According to the Invention 230 mg of microparticles obtained in step 2 of Example 8, 100 mg of crushed and sieved Amberlite IR69F (sodium polystyrenesulfonate), 70 mg of sieved Polyox WSR 303 Sentry (polyethylene oxide), 3.8 mg of magnesium stearate and 1.9 mg of Aerosil 200 (colloidal silica) are introduced into a size 0 gelatin capsule.

Figure 5:
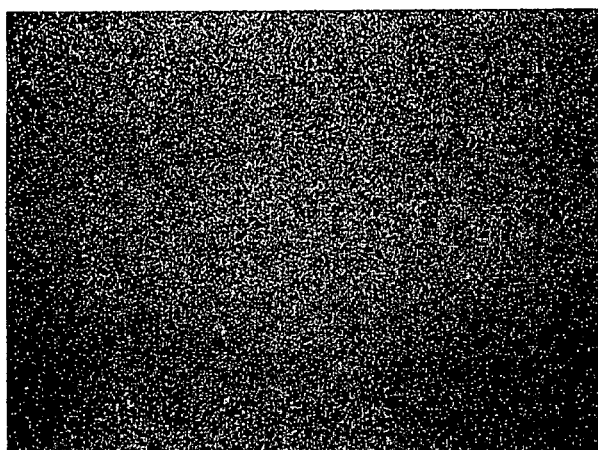
FIG. 5 shows photographs of the contents of a capsule according to Example 9, observed with the naked eye (A) and under an optical microscope (B).
Figure 5:
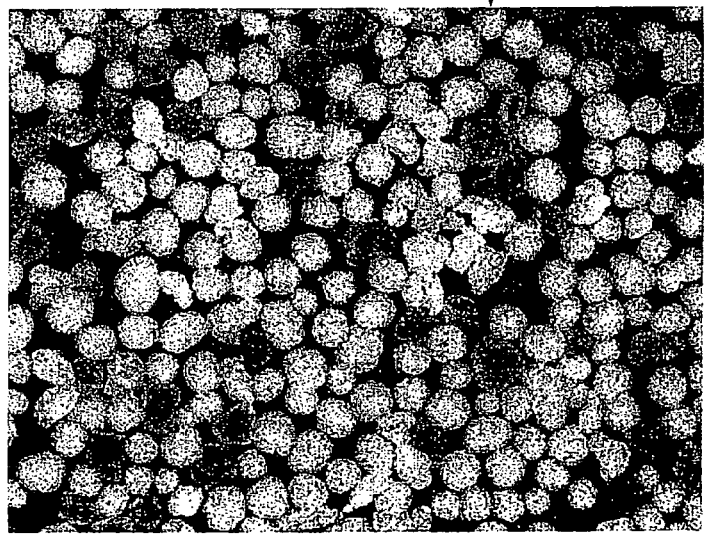

As shown in FIG. 5, observed with the naked eye (A) and under an optical microscope (B), the microparticles of active principle and the microparticles of viscosifiers are:

indistinguishable,
inseparable by sieving.

Example 10

Crushing of the Contents of a Capsule Prepared According to Example 9

The contents of the capsule prepared in Example 9 are crushed for 2 minutes in a mortar and pestle.

Figure 6:
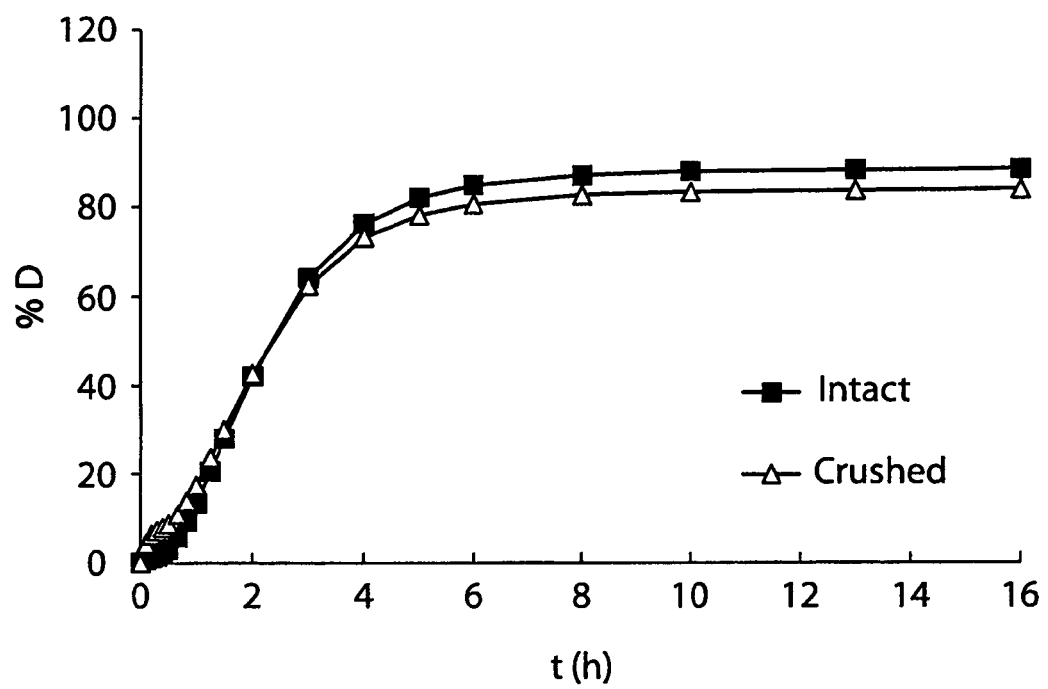
FIG. 6 shows the release profile of crushed microparticles (blank triangle) or intact microparticles (ailled square) of Example 9.

The release profiles of the crushed microparticles are shown in FIG. 6. The release profile is determined under the conditions of the reference dissolution test.

The release profiles of the intact and crushed products are similar. Thus crushing has little or even no effect on the release of the oxycodone from the microparticles.

Example 11

Test for Syringe Extraction of the Contents of a Capsule Prepared According to Example 9

A capsule prepared according to Example 9 is opened and the contents are crushed for 2 minutes with a mortar and pestle and then mixed for 10 min with 2.5 ml of extraction liquid at ambient temperature (A) or at the boil (B). The solution is then taken up with a 2.5 ml syringe (with either an 18G needle or a 27G needle) through cotton wool serving as a filter. The amount of oxycodone HCl extracted is analyzed by HPLC or UV and is shown in Tables 5 and 6.

The low extraction yields observed (<20%) are totally dissuasive for potential misusers.

Example 12

Test for Extraction of the Contents of a Capsule According to Example 9 into Drinks A capsule prepared according to Example 9 is opened and the contents are crushed for 2 minutes with a mortar and pestle and then mixed with 100 ml of non-alcoholic drink or 50 ml of alcoholic drink as indicated in the Table below:

| Solvent | Volume (ml) |
| --- | --- |
| Tap water | 100 |
| Tap water with 2 g/l of NaCl | 100 |
| pH 1.2 (HCl) with 2 g/l of NaCl | 100 |
| Sprite ® | 100 |
| Pepsi-Cola ® | 100 |
| Smirnoff Twisted Apple (5% alcohol) | 100 |
| Absolut ® vodka (40% alcohol) | 50 |

The solution is then taken up and the amount of oxycodone HCl extracted is analyzed by HPLC or UV and is shown in Table 7.

The low extraction yields observed, even for long extraction times, are totally dissuasive for potential misusers.

TABLE 1

(Example 4)

| | % oxycodone HCl extracted with the 18 G syringe | |
|---|---|---|
| | Liquid at ambient temperature | Liquid at the boil |
| Tap water | 0.2 | 1 |
| Water/ethanol (60/40 v/v) | 3 | 8 |
| Ethanol | 18 | 1 |

TABLE 2

(Example 5)

| | % oxycodone HCl extracted with the 18 G syringe | |
|---|---|---|
| | Liquid at ambient temperature | Liquid at the boil |
| Tap water | 1 | 2 |
| Water/ethanol (60/40 v/v) | 4 | 7 |
| Ethanol | 19 | 8 |

TABLE 3

(Example 6)

| | % oxycodone HCl extracted with the 18 G syringe | |
|---|---|---|
| | Liquid at ambient temperature | Liquid at the boil |
| Tap water | 1 | 2 |
| Water/ethanol (60/40 v/v) | 5 | 8 |
| Ethanol | 19 | 9 |

TABLE 4

(Example 7)

| | % oxycodone HCl extracted with the 18 G syringe | |
|---|---|---|
| | Liquid at ambient temperature | Liquid at the boil |
| Tap water | 0.5 | 2 |
| Water/ethanol (60/40 v/v) | 4 | 10 |
| Ethanol | 19 | 2 |

TABLE 5

Amount of AP extracted (%) using a 2.5 ml syringe equipped with a 27 G needle (Example 11)

| | % oxycodone HCl extracted with the 27 G syringe | |
|---|---|---|
| | Liquid at ambient temperature | Liquid at the boil |
| Tap water | 0 | 1 |
| Water/ethanol (60/40 v/v) | 0 | 4 |
| Absolute ethanol | 14 | 0 |

TABLE 6

Amount of AP extracted (%) using a 2.5 ml syringe equipped with an 18 G needle (Example 11)

| | % oxycodone HCl extracted with the 18 G syringe | |
|---|---|---|
| | Liquid at ambient temperature | Liquid at the boil |
| Tap water | 0 | 1 |
| Water/ethanol (60/40 v/v) | 3 | 8 |
| Absolute ethanol | 18 | 1 |

TABLE 7

Amount of AP extracted (%) from different drinks as a function of time (Example 12)

| | extraction time | |
|---|---|---|
| Solvent | 1 h | 21 h |
| Tap water | 8 | <45 |
| Tap water with 2 g/l of NaCl | 8 | <45 |
| pH 1.2 (HCl) with 2 g/l of NaCl | 14 | <45 |
| Sprite ® | 3 | <45 |
| Pepsi-Cola ® | 3 | <45 |
| Smirnoff Twisted Apple (5% alcohol) | 23 | <45 |
| Absolut ® vodka (40% alcohol) | 24 | <45 |

The invention claimed is:

1. A method of preparing a pharmaceutical formulation for combating the misuse of active principle (AP), the method comprising:
    providing inert cores;
    coating the inert cores with at least one layer comprising the active principle;
    coating the at least one layer comprising the active principle with at least one coating layer (Ra) to create modified release coated microparticles resistant to crushing;
    wherein said at least one coating layer (Ra) represents a fraction by weight (Tp) greater than 30%, expressed in % by dry weight, based on the total weight of the coated microparticles,
    whereby said at least one coating layer (Ra) comprises:
        at least one film-forming (co)polymer (A1) insoluble in the gastrointestinal juices present in a proportion of 60% to 90% by weight on a dry basis, relative to the total mass of the coating composition;
        at least one (co)polymer soluble in the gastrointestinal juices (A2) present in a proportion of 5% to 40% by weight on a dry basis, relative to the total mass of the coating composition; and
        at least one plasticizer (A3) present in a proportion of 1% to 30% by weight on a dry basis, relative to the total mass of the coating composition; and
    wherein said formulation further comprises at least one viscosifier (Vb) whereby said formulation further comprises at least one AP sequestering agent Q, whereby a complex with the AP is formed in solution.

2. The method of claim 1, whereby said at least one film-forming (co)polymer (A1) is selected from the group consisting of: water-insoluble cellulose derivatives, ethyl cellulose, cellulose acetate, acrylic polymers, copolymers of (meth) acrylic acid alkyl ester, copolymers of acrylic and methacrylic acid esters carrying at least one quaternary ammonium group, copolymers of alkyl (meth)acrylate and trimethylammonioethyl methacrylate chloride), polyvinyl acetates, and mixtures thereof;

whereby said at least one (co)polymer soluble in the gastrointestinal juices (A2) is selected from the group consisting of: nitrogen-containing (co)polymers, polyacrylamides, poly-N-vinylamides, polyvinylpyrrolidones (PVP), poly-N-vinyllactams, water-soluble cellulose derivatives, polyvinyl alcohols (PVA), polyalkylene oxides, polyethylene oxides (PEO), polyethylene glycols (PEG), and mixtures thereof;

whereby said at least one plasticizer (A3) is selected from the group consisting of: cetyl alcohol esters, glycerol, glycerol esters, acetylated glycerides, glycerol monostearate, glyceryl triacetate, glycerol tributyrate, phthalates, dibutyl phthalate, diethyl phthalate, dimethyl phthalate, dioctyl phthalate, citrates, acetyl tributyl citrate, acetyl triethyl citrate, tributyl citrate, triethyl citrate, sebacates, diethyl sebacate, dibutyl sebacate, adipates, azelates, benzoates, vegetable oils, fumarates, diethyl fumarate, malates, diethyl malate, oxalates, diethyl oxalate, succinates, dibutyl succinate, butyrates, cetyl alcohol esters, salicylic acid, triacetin, malonates, diethyl malonate, castor oil, and mixtures thereof.

3. The method of claim 1, whereby said at least one coating layer (Ra) further comprises at least one surfactant, lubricant, mineral or organic filler (A4) in the following amount (in % by weight, based on the total weight of the coating):

$$0 \leq A4 \leq 40.$$

4. The method of claim 3, whereby said at least one surfactant, lubricant, mineral or organic filler (A4) is selected from the group consisting of: anionic surfactants, alkali metal, alkaline earth metal salts of fatty acids, stearic acid, oleic acid, non-ionic surfactants, polyethoxylated oils, polyethoxylated hydrogenated castor oil, polyoxyethylene/polyoxypropylene copolymers, polyethoxylated sorbitan esters, polyethoxylated castor oil-based compound, stearates, calcium stearate, magnesium stearate, aluminum stearate, zinc stearates, stearylfumarates, sodium stearylfumarate, glycerol behenates, talcum, colloidal silica, titanium oxide, magnesium oxide, bentonite, microcrystalline cellulose, kaolin, aluminum silicate, and mixtures thereof.

5. The method of claim 1, whereby said coated microparticles have a mean diameter between 100 and 600 μm less than or equal to 1000 μm.

6. The method of claim 1, whereby said formulation is in the form of a tablet, and whereby said coated microparticles comprise at least one outer coating composed of at least one deformable organic constituent with a melting point of between 40° C. and 120° C.

7. The method of claim 6, whereby said at least one outer coating represents from 5 to 50% of the total weight of the said coated microparticles of AP by dry weight.

8. The method of claim 1, whereby said at least one viscosifier (Vb) is soluble in at least one of the following solvents: water, alcohols, ketones and mixtures thereof.

9. The method of claim 8, whereby said at least one viscosifier (Vb) is selected from the group consisting of: polyacrylic acids, polyacrylic acids derivatives, polyalkylene glycols, polyethylene glycol, polyalkylene oxides, polyethylene oxides, polyvinylpyrrolidones, gelatins, polysaccharides, sodium alginate, pectins, guars, xanthans, carrageenans, gellans, cellulose derivatives, hydroxypropyl methyl cellulose, methyl cellulose, hydroxyethyl cellulose, carboxymethyl cellulose, and mixtures thereof.

10. The method of claim 8, whereby said at least one viscosifier (Vb) is a polyoxyethylene with an average molecular weight of 1 million g/mol to 8 million g/mol.

11. The method of claim 1, whereby at least part of said viscosifier (Vb) is in the form of microparticles that are distinct from the microparticles comprising the AP, and inseparable by sieving from the microparticles of AP.

12. The method of claim 1, whereby said at least one AP sequestering agent Q consists of a salt containing at least one ion that forms a complex with the extracted AP salt in solution.

13. The method of claim 12, whereby said at least one ion is an organic ion with opposite polarity to that of the AP in solution.

14. The method of claim 12, whereby said at least one AP sequestering agent Q comprises a salt selected from the group consisting of:

anionic organic salts, carboxymethyl cellulose, carboxymethyl cellulose derivatives, crosslinked carboxymethyl cellulose, crosslinked carboxymethyl cellulose derivatives, polysaccharides, phosphates, trisilicates, saponified fatty acids, self-emulsifying glyceryl monooleates, polyamino acids, proteins, peptides, cationic metallic salts, cationic organic salts, cationic polymers, and mixtures thereof.

15. The method of claim 12, whereby said at least one AP sequestering agent Q is a salt that is either a strongly acidic cation exchange resin when the AP is cationic, or a strongly basic anion exchange resin when the AP is anionic.

16. The method of claim 15, wherein said at least one AP sequestering agent Q comprises a styrene/divinylbenzene copolymer.

17. The method of claim 15, wherein said at least one AP sequestering agent Q comprises a sulfonated styrene/divinylbenzene copolymer.

18. The method of claim 15, wherein said at least one AP sequestering agent Q comprises a styrene/divinylbenzene copolymer carrying quaternary ammonium groups.

19. The method of claim 15, wherein said at least one AP sequestering agent Q comprises a crosslinked methacrylic acid/divinylbenzene copolymer or one of its salts.

20. The method of claim 15, wherein said exchange resin comprises a phenolic polyamine.

21. The method of claim 11, whereby at least part of said viscosifier (Vb) is in the form of microparticles that are distinct from the microparticles comprising the AP, whereby said at least one AP sequestering agent Q is in the form of microparticles that are distinct from the microparticles comprising the AP and whereby said microparticles of Vb and said microparticles of Q are inseparable by sieving from the microparticles of AP.

22. The method of claim 11, whereby said formulation further comprises at least one excipient in a free state.

23. The method of claim 22, whereby said at least one excipient is selected from the group consisting of: calcium stearate, glycerol palmitostearate, magnesium oxide, polyalkylene glycols, polyethylene glycols, polyvinyl alcohol, sodium benzoate, stearic acid, maize starch, talcum, colloidal silica, zinc stearate, magnesium stearate, stearylfumarate, and mixtures thereof.

24. The method of claim 1, whereby said formulation further comprises immediate release AP.

25. The method of claim 1, whereby said at least one AP is selected from the group consisting of: amphetamines, narcotics, anorexigenics, antidepressants, antiepileptics, antiparkinsonism substances, anxiolytics, barbiturates, benzodiazepines, hypnotics, neuroleptics, opioids, psychostimulants, psychotropic substances and mixtures thereof.

26. The method of claim 1, whereby said at least one AP is selected from the group consisting of: anileridine, acetorphine, acetyl-alpha-methylfentanyl, acetyldihydrocodeine, acetylmethadol, alfentanil, allylprodine, alpha-cetylmethadol, alpha-meprodine, alpha-prodine, alpha-methadol, alpha-methylfentanyl, alpha-methylthiofentanyl, atropine, butorphanol, benzethidine, benzylmorphine, beta-hydroxyfentanyl, beta-hydroxy-methyl-3-fentanyl, beta-cetylmethadol, beta-meprodine, beta-methadol, beta-prodine, bezitramide, buprenorphine, dioxaphetyl butyrate, clonitazene, cyclazocine, cannabis, cetobemidone, codeine, coca, cocaine, codoxime, dezocine, dimenoxadol, dipipanone, desomorphine, dextromoramide, dextropropoxyphene, diampromide, diethylthiambutene, difenoxin, dihydrocodeine, dihydroetorphine, dihydromorphine, dimenoxadol, dimepheptanol, dimethylthiambutene, diphenoxylate, drotebanol, eptazocine, ethoheptazine, ethylmethylthiambutene, ethylmorphine, etonitazene, ecgonine, ephedrine, etorphine, etoxeridine, fentanyl, furethidine, heroin, hydrocodone, hydromorphinol, hydromorphone, hydroxypethidine, isomethadone, ketobemidone, levallorphan, lofentanil, levomethorphan, levomoramide, levophenacylmorphan, levorphanol, meptazinol, meperidine, metazocine, methadone, methyldesorphine, methyldihydromorphine, methylphenidate, methyl-3-thiofentanyl, methyl-3-fentanyl, metopon, moramide, morpheridine, morphine, myrophine, nalbuphine, narceine, nicomorphine, norlevorphanol, normethadone, nalorphine, normorphine, nicocodine, nicodicodine, nicomorphine, noracymethadol, norcodeine, norpipanone, opium, oxycodone, oxymorphone, papaveretum, phenadoxone, phenoperidine, promedol, properidine, propiram, propoxyphene, parafluorofentanyl, pentazocine, pethidine, phenampromide, phenazocine, phenomorphan, pholcodine, piminodine, piritramide, proheptazine, propanolol, racemethorphan, racemoramide, racemorphan, remifentanil, sufentanil, thebacon, thebaine, thiofentanyl, tilidine, trimeperidine, tramadol, their pharmacologically acceptable salts, esters, hydrates, polymorphs and isomers, and mixtures thereof.

27. The method of claim 1, whereby said at least one AP is selected from the group consisting of: oxycodone hydrochloride, morphine sulfate, oxymorphone hydrochloride, hydromorphone hydrochloride, hydrocodone hydrochloride, tramadol hydrochloride, and mixtures thereof.

28. The method of claim 1, whereby said formulation does not contain an AP antagonist.

29. The method of claim 1, whereby said formulation comprises at least two different populations of coated microparticles of AP, whereby each population of coated microparticles has different release kinetics.

30. The method of claim 1, wherein the inert cores are inert cellulose beads.

31. The method of claim 1, wherein coating the inert cores with at least one layer comprising the active principle is by spray-coating.

* * * * *